United States Patent
Schneider et al.

(10) Patent No.: US 6,992,208 B2
(45) Date of Patent: Jan. 31, 2006

(54) PROCESS FOR THE SYNTHESIS OF IODOPROPYNYL BUTYLCARBAMATE IN AN AQUEOUS SOLUTION OF A SUITABLE SURFACTANT

(75) Inventors: David J. Schneider, Union, KY (US); Charles A. Schneider, Villa Hills, KY (US); Kurt A. Jones, Cold Springs, KY (US); Martin S Heineke, Cincinnati, OH (US)

(73) Assignee: H&S Chemical Company, Inc., Covington, KY (US)

( * ) Notice: Subject to any disclaimer, the term of this patent is extended or adjusted under 35 U.S.C. 154(b) by 67 days.

(21) Appl. No.: 10/634,462

(22) Filed: Aug. 4, 2003

(65) Prior Publication Data

US 2005/0033083 A1    Feb. 10, 2005

(51) Int. Cl.
*C07C 269/00*    (2006.01)

(52) U.S. Cl. ..................................... 560/167
(58) Field of Classification Search ................ 560/167
See application file for complete search history.

(56) References Cited

U.S. PATENT DOCUMENTS

| 3,923,870 A | 12/1975 | Singer |
| 4,297,258 A | 10/1981 | Long, Jr. |
| 5,693,849 A | 12/1997 | Nowak |

FOREIGN PATENT DOCUMENTS

EP    0014032    8/1980

*Primary Examiner*—Paul A. Zucker
(74) *Attorney, Agent, or Firm*—Fay, Sharpe, Fagan, Minnich & McKee, LLP

(57) ABSTRACT

A process for the manufacture of iodopropynyl butylcarbamate (IPBC) is disclosed wherein the subject reaction is carried out in an aqueous solution of a suitable surfactant. The iodination reactant is metallic iodide salt which serves as a donor of I+ ions. The I+ ion is generated on an as needed basis, during the reaction sequence, hence the formation of undesirable isomers of IPBC are minimized. The process of this invention produces a highly purified IPBC having, preferably, a low moisture content (wet-cake). The IPBC produced by such a process is also disclosed herein.

18 Claims, No Drawings

PROCESS FOR THE SYNTHESIS OF IODOPROPYNYL BUTYLCARBAMATE IN AN AQUEOUS SOLUTION OF A SUITABLE SURFACTANT

BACKGROUND OF THE INVENTION

This invention is concerned with processes for the production of iodopropynyl butylcarbamate (CAS NO. 55406-53-6), synonyms, 3-iodo-2-propynyl butylcarbamate; 3-iodo-2-propynyl n-butylcarbamate; 3-iodopropynyl butylcarbamate; ASC 67000; iodo-2-propynyl butylcarbamate; and iodopropynyl butylcarbamate, hereinafter collectively referred to as "IPBC." The invention also includes the IPBC generated by these processes.

In the last several decades, IPBC has achieved widespread use as a biocide and as a fungicide. As to these usages, the use of IPBC as a fungicide has become paramount. As a fungicide, IPBC has achieved wide acceptance as a paint additive. The build up of fungus on painted surfaces is a troublesome problem particularly in southern climates. In order to prevent an unsightly appearance, particularly on outdoor painted surfaces, this fungus must be scrubbed off of the painted surface. If a small percentage of IPBC is added to the paint during it's manufacture, the development and buildup of fungus on the painted surface is eliminated.

In addition to use in paints, IPBC has achieved widespread commercial acceptance as a fungicide for treating lumber. Further, IPBC is useful as an additive for cosmetics where it functions as both a biocide and as a fungicide in order to prevent the undesirable buildup of bacteria and fungi in cosmetic formulations.

IPBC is also added to polymeric formulations in order to prevent bacterial and fungi buildups on articles which are manufactured from the polymers.

For use in paint and cosmetics, it is desirable to have the IPBC as pure as possible, as pure IPBC is a white powder. In contrast, closely related impurities such as di- and tri-iodo compounds are colored and hence tend to tint the paint and cosmetic formulations. This tinting is very undesirable.

Metal cutting fluids tend to be used for extended periods of time. It has been known for many decades that bacterial build in these cutting fluids is undesirable from an odor point of view and from a functionality point of view. The build up of bacterial and fungicidal residue in these cutting fluids tends to detrimentally affect the lubricating properties of these cutting fluids. IPBC has also found widespread acceptance as a biocide in cutting fluids.

In the manufacture of IPBC, it is desirable to produce IPBC with the lowest possible moisture content. The process of the present invention produces a wet-cake having a very low moisture content. This low moisture content results from a superior crystalline structure.

Purity is of the utmost importance in the formation of IPBC, as impurities in IPBC tend to discolor the product. These impurities are further thought to make the IPBC more light sensitive. This light sensitivity is very important, as light degrades IPBC to an off white in color and hence makes it unsuitable for use in color sensitive products such as paint and cosmetics.

Further it is desirable to have the IPBC as pure as possible as it is often necessary to obtain regulatory approval for the use of IPBC in products such as paint and cosmetics. High concentrations of impurities in the IPBC present substantial problems as these impurities have individual and distinct toxicity profiles which must be dealt with in any approval procedure. The present invention relates to processes for the production of high yields of IPBC with low concentrations of impurities.

In this regard, processes for producing iodo alkynyl carbamates are known. For example, U.S. Pat. No. 5,693,849, issued on Dec. 2, 1997 (the '849 patent), relates to a process for producing iodo alkynyl carbamates. The process is carried out in an aqueous environment which comprises an aqueous solution of a surfactant, which can be either an acidic organic phosphate partial ester or a sulfated fatty alcohol. These are ionic surfactants. A alkynyl carbamate is dispersed in the aqueous reaction medium and iodinated with iodine in the presence of sodium hypochlorite. Among other things, the process of the present invention is distinct from the process of the '849 patent in that, in the subject invention, the surfactant is preferably nonionic. Further, the surfactant used in the '849 process are of two carefully defined classes of phosphated or sulfated compounds, and lastly the carbamate is iodinated with elemental iodine. Specific surfactants are stated to be required for the reaction of the carbamate with elemental iodine.

The production and use of IPBC is also discussed in U.S. Pat. No. 3,923,870. The process for preparing IPBC disclosed in that patent requires an initial preparation of iodopropargyl alcohol. This is a dangerous compound that must be isolated by extraction in ethyl ether. The ether then must be evaporated to yield the pure alcohol product. Iodopropargyl alcohol, is not only extremely corrosive to the skin, but also decomposes, possibly violently, at a temperature of about 125° C. so it must be very carefully handled. To form the final IPBC product, the iodopropargyl alcohol is then reacted with butyl isocyanate, which also is a strong irritant. The IPBC prepared by this process is very impure, and has a distinct odor. Further, the resultant IPBC must be further processed for purification.

EPO Publication No. 0014032 also describes a method of preparing IPBC. In this disclosure, propargyl alcohol is first reacted with an isocyanate, e.g., butyl isocyanate, to form propargyl butylcarbamate. The resulting propargyl butylcarbamate is then reacted with a slight molar excess of an iodinating agent such as a mixture of pure iodine, an alkali metal hydroxide and sodium hypochlorite in an aqueous medium, typically containing a co-solvent. To promote sufficient contact between the sparingly water-soluble alkynyl carbamate and the iodinating agent, the reaction preferably is conducted in the presence of a water miscible auxiliary solvent such as an alcohol, i.e., is an aqueous methanol solution. The method of isolating the end product is by extraction from the aqueous methanol solution. This disclosure also suggests conducting the reaction in an aqueous medium by initially dispersing or emulsifying the alkynyl carbamate, with the aid of a surfactant, but does not indicate the ultimate method of product isolation, the yield, nor the purity of the product made in this manner. Surfactants disclosed as being suitable for use, include hydrolyzed or partially hydrolyzed polyvinyl acetates, phase-transfer catalysts such as cetyl trimethyl ammonium bromide, dispersing agents such as the sodium salt of a condensate of formaldehyde and naphthalene sulfonic acid and emulsifying agents such as ethoxylated nonyl phenols.

In the EP publication, the presence of the iodopropynyl butylcarbamate is ascertained merely by infrared (IR) spectra. Viewed in the light of present day requirements, both commercial and regulatory, this data does not document the completion of the reaction. The appearance of an infrared absorption band at 2200 cm.sup.-1 also does not indicate the yield or the purity of the end product.

U.S. Pat. No. 4,297,258 also describes the reaction of propynyl butylcarbamate with iodine in an aqueous medium containing a co-solvent. The product is extracted from the reaction mixture with a water immiscible organic solvent.

Consequently, it would be desirable to produce high purity IPBC compound without the limitations (i.e., water content, etc.) set forth above.

BRIEF DESCRIPTION OF THE INVENTION

In one aspect, the subject invention relates to the production of a iodinated carbamate by the reaction of a carbamate with the I+ ion, wherein the I+ ion is generated from iodide salt in the presence of a strong base. The reaction is carried out in an aqueous solution of a suitable surfactant. In a more preferred embodiment, IPBC is produced by the reaction of propynyl butylcarbamate, with I+ ion. The I+ ion is generated by the reaction of sodium hypochlorite with sodium iodide. The composite reaction is carried out in an aqueous solution which incorporates a suitable wetting agent.

The process of this invention results in a high yield of IPBC, having minimum di and tri iodinated carbamates. Further, the resulting IPBC has a substantially lower wet-cake moisture content.

These and other aspects and/or objects of the invention will, in part, be obvious and, in part, pointed out in more detail below. Additionally, the invention accordingly comprises the several steps and the relation of one or more of such steps with respect to each of the others and the articles possessing the features, properties, and the relation of elements exemplified in the following detailed disclosure.

DETAILED DESCRIPTION OF THE PREFERRED EMBODIMENTS

This invention is concerned with a process for the production of high purity IPBC. In a broad sense this invention relates to a process for the production of IPBC by the iodination of propynyl butylcarbamate with a source of I+ ions, wherein the pH, reaction temperatures and reaction sequence is carefully controlled. The I+ ion is produced, on an as needed basis, by the oxidation of a metallic iodide salt.

High purity IPBC is produced having minimal di- and tri-iodinated isomer impurities. Further, the IPBC has very low wet cake moisture content. The reaction of the subject invention is carried out in a solution of a suitable surfactant, however nonionic surfactants, or aqueous solutions of nonionic surfactants, are preferred.

In the process of this invention, a suitable reaction vessel is charged with a solution of a suitable surfactant. Examples of suitable surfactants are compounds such as alcohol ethoxiates. A preferred nonionic surfactant for use in the process of this invention is MERPOL HCS sold by the Stephan Chemical Company (Merpol HCS is thought to be a low molecular weight capped ethylene glycol polymer of about 20 units). While water is the preferred media for the reaction, other solvents can be used. The concentration of the surfactant in the solvent can be from about 15 to about 20 weight percent, a more preferred range is from about 17 to about 20 weight percent, with a most preferred range being from about 18 to about 20 weight percent. A most preferred concentration for the surfactant is 20 weight percent. All concentrations are based on the weight of the PBC charge.

In this regard, PBC relates to n-butylproparglyl carbamate (CAS NO. 76114-73-3), also known as n-propynyl butylcarbamate.

In the reaction, a suitable reactor is charged with an amount of the surfactant solution and the charge is cooled to a temperature of from about 0 to about 8° C. or to a temperature of from about 0 to about 12° C.; a more preferred range for this temperature is from about 5 to about 12° C., with a most preferred range being from about 8 to about 10° C. and a most preferred operating temperature being 9° C. If these temperature parameters are varied, the yield and quality of the IPBC formed may be adversely affected.

To this cooled solution is added an aqueous solution of metal iodide salt, suitable iodide salts are sodium iodide, and potassium iodide. The pH of the reaction mass is then adjusted to greater than 7.

The above set forth pH adjustment is effected with an excess of suitable basic material. It is preferred that the pH adjustment to greater than 7.0 and that it be effected with an alkali metal hydroxide. For this purpose sodium hydroxide and potassium hydroxide are preferred.

The reactor must have a molar ratio of alkali to match the molar concentrations of n-propynyl butylcarbamate which will be subsequently charged to the reactor mass. From about 0.8 to about 1.0 moles of alkali per mole of n-propynyl butylcarbamate should be provided.

To the reaction mass is added a molar amount of propynyl butylcarbamate which is the basis for other charges as discussed herein.

The reaction mass is then charged with an oxidizing agent. The preferred oxidizing agent is sodium hypochlorite, however other oxidizing agents such as potassium hypochlorite and hydrogen peroxide can be used.

The function of the oxidizing agent is to oxidize the iodide salt to the I+ ion.

From about 1.10 to about 1.3 moles of the oxidizing agent is then added to the reaction mass. This charge is based on the molar charge of the iodide salt. The preferred oxidizing agent is sodium hypochlorite, with the preferred concentration being 1.2 moles of oxidizing agent per mole of iodide salt.

During this reaction time the I+ ion is generated on an as needed basis by the oxidation of the metallic iodide salt. This production of the I+ ion on an as needed basis results in higher yields of purer IBPC. This production of the I+ ion on as needed basis prevents the formulation of undesirable impurities as competitive undesirable reactions are kept to a minimum.

During the addition of the oxidizing agent the temperature of the reaction mass is maintained at a temperature of from about 0 to about 11° C., a more preferred range is from about 4 to about 11° C. with a most preferred temperature being 9° C. Again it may be possible to operate the subject reaction outside of these temperature parameters however, the quality and yield of the IPBC may be adversely affected.

The oxidation reaction is exothermic. During the oxidation sequence the temperature must not be allowed to ramp up beyond the ranges as listed above. Therefore, the rate at which the oxidizing agent is added to the reaction mass is controlled by the efficiency and capacity of the cooler in the reaction vessel.

With the addition of the oxidizing agent the reaction is essentially complete. While agitating, the reaction mass is allowed to slightly increase in temperature, to allow for complete iodination of the propynyl butylcarbamate. At this stage of the reaction the temperature should not exceed 20° C. The temperature usually ranges from about 15 to about 20° C. If the temperature at this stage of the reaction exceeds 20° C. the quality of the resulting IPBC is adversely affected While stirring, the reaction is allowed to proceed for a period of time of from about 30 to about 180 minutes; in an embodiment, the reaction proceeds for from about 60 to about 120 minutes. A most preferred reaction time is 90 minutes. Reaction times of longer than 180 minutes result in lower yield and quality of the resulting IPBC is adversely affected. If the reaction time is allowed to exceed 180 minutes, some of the iodine may be stripped off of already formed IPBC producing off colored and undesirable isomers.

At this point, the conversion of propynyl butylcarbamate to IPBC is essentially complete. The temperature of the reaction mass is then allowed to ramp up to a temperature of from about 35 to about 40° C. at a rate of from about 0.25 to about 1.0 degrees per minute or a rate of from about 0.25 to about 0.75 degrees per minute.

The pH of the reaction mass is then adjusted with an organic acid such that the pH of the reaction mass is slightly acidic. In one embodiment, the reaction mass is adjusted to a pH of about 6.9 with an organic acid, preferably with acetic acid. The pH is then adjusted to about 6.6 using a mild acid buffer such as sodium bisulfite.

The temperature of the reaction mass is allowed to further ramp up to a temperature of from about 55 to about 59° C. with a most preferred range being from about 55 to about 56° C. This temperature ramp up is effected at a rate of from about 0.25 to about 0.75 degrees per minute.

When this ramp up in temperature is effected to the desired range, the temperature of the reaction mass is immediately ramped downward to a range of between 20 and 30° C. or more preferably a range of between 25 and 30° C., with a most preferred temperature being 25° C. The ramping down of the temperature is effected at a rate of from about 0.25 to about 0.75° C. per minute or from about 0.35 to about 0.75° C. per minute. Agitation continues during this ramp down.

The temperature selected for this ramp down is then maintained for a minimum holding period of about 10 minutes.

After the holding period the reaction mass is filtered and washed with water. The wash water can be between 10 and 30° C. The preferred temperature for the wash water is 30° C.

The filter cake, is essentially IPBC and is dried at an effective temperature to a constant weight. The preferred drying temperature is between 25 and 45° C.

As is evident to one skilled in the art from the above description the temperatures of the various reaction steps are varied throughout the composite reaction sequence. These temperature variations affect the crystalline structure of the resulting IPBC. As a result of these crystalline changes, the IPBC in the final filter cake is able to retain less moisture with the result that superior IPBC, having less retained water is produced.

The subject process of the present invention comprise one or more pertinent steps:
1. Carrying the reaction out in the presence of a suitable wetting agent;
2. Producing a reactive I+ ion by the oxidation of an alkali metal iodide salt;
3. Acid adjusting the pH; and,
4. Cycling the temperature during the various reaction sequence so as to produce a crystalline structure in the resulting IPBC, which retains minimal moisture.

The subject invention is further described by reference to the following examples. These examples are intended to illustrate the feature of the subject invention and should not be construed in any way was limiting the invention which is defined by the below set forth claims.

EXAMPLE 1

A reactor was charged with 330 g of water which was then cooled to a temperature of 0–8° C.

To the cooled water, while stirring was added 3.4 grams of a nonionic surfactant agent Merpol HCS and 16.85 g of butyl propynyl carbamate while maintaining the temperature between 0–8° C.

The reactor was further charged with 8.85 g of a 50% aqueous solution of sodium hydroxide and 16.28 grams of sodium iodide which had been previously dissolved in 50 g of water. The temperature was maintained between 5–8° C.

The reactor with strong agitation was slowly charged with 70.2 g of a 13.6% solution of sodium hypochlorite while maintaining the reaction mass at a temperature of between 6 and 11° C.

The temperature was allowed to ramp up slightly to 15–20° C. and the reaction mass was agitated for 90 minutes. The reaction mass was then slowly heated to a temperature of 35–40° C. The ramping up of the temperature was effected at a rate of 0.25 to 0.75° C. per minute.

With agitation the pH of the reaction mass was then adjusted to 6.9 with acetic acid. The pH reaction mass was then adjusted to 6.6 with sodium bisulfite. The temperature was then ramped up to 55 to 59° C. at a rate of 0.25 to 0.75° C. per minute.

When a temperature reached a range of 55–59° C. cooling was applied to the reaction mass to ramp the temperature of the reaction mass down to 25–30° C., at a ramp down rate of 0.33–0.75° C. per minute.

The reaction mass was then agitated for 10 minutes and then the reaction mass was filtered. The filtration cake was washed twice with 100 ml of water. The cake was then dried at 35° C. to a constant weight. The reaction achieved a yield of 93.5% of IPBC which assayed at 98.7% IPBC.

EXAMPLE 2

The reaction procedure of Example 1 was repeated except that in the iodination step potassium iodide was substituted for sodium iodine. The procedure produced IPBC at a yield of 93.5% wherein the resulting IPBC assayed at 98.7%.

EXAMPLE 3

A reactor was charged with 1400 gal of water which was then cooled to a temperature of 0–8° C.

To the cooled water, while stirring was added to 87 pounds of a nonionic surfactant agent Merpol HCS and 429 pounds of butyl propynyl carbamate while maintaining the temperature between 0–8° C.

The reactor was further charged with 214 pounds of a 50% aqueous solution of sodium hydroxide and 853 pounds of 50% sodium iodide solution. The temperature was maintained between 5–8° C.

The reactor with strong agitation was slowly charged with 1780 pounds of a 13.6% solution of sodium hypochlorite while maintaining the reaction mass at a temperature of between 6 and 11° C.

The temperature was allowed to ramp up slightly to 15–20° C. and the reaction mass was agitated for 90 minutes. The reaction mass was then slowly heated to a temperature of 35–40° C. The ramping up of the temperature was effected at a rate of 0.25 to 0.75° C. per minute.

With agitation the pH of the reaction mass was then adjusted to 6.9 with acetic acid. The pH reaction mass was then adjusted to 6.6 with sodium bisulfite. The temperature was then ramped up to 55 to 59° C. at a rate of 0.25 to 0.75° C. per minute.

With agitation the pH of the reaction mass was then adjusted to 6.9 with acetic acid. The pH reaction mass was then adjusted to 6.6 with sodium bisulfite. The temperature was then ramped up to 55 to 59° C. at a rate of 0.25 to 0.75° C. per minute.

When a temperature reached a range of 55–59° C., cooling was applied to the reaction mass to ramp the temperature of the reaction mass down to 25–30° C., at a ramp down rate of 33–75° C. per minute.

When a temperature reached a range of 55–59° C., cooling was applied to the reaction mass to ramp the temperature of the reaction mass down to 25–30° C., at a ramp down rate of 33–75° C. per minute.

The reaction mass was then agitated and then the reaction mass was centrifuged with water for 10 minutes. The cake was washed. The cake was then dried at 30–45° C. to a constant weight. The reaction achieved a yield of 93.2% of IPBC which assayed at 98.7% IPBC.

The foregoing description is, at present, considered to be the preferred embodiments of the present invention. However, it is contemplated that various changes and modifications apparent to those skilled in the art, may be made without departing from the present invention. Therefore, the foregoing description is intended to cover all such changes and modifications encompassed within the spirit and scope of the present invention, including all equivalent aspects.

What is claimed is:

1. A process for the production of 3-iodo-2-propynyl butylcarbamate, which comprises the steps of:
   a. charging a reactor with an aqueous solution of a nonionic surfactant,
   b. cooling the reaction mass to a temperature of from about 0° C. to about 12° C.,
   c. adding to the reaction mass an aqueous solution of a metallic iodide salt,
   d. adjusting the pH of the reaction mass to greater than 7 with a molar excess of an alkali metal hydroxide, wherein the molar excess is based on the propynyl butylcarbamate to be added,
   e. charging the reaction mass with an effective amount of propynyl butylcarbamate,
   f. charging the reaction mass with a solution of an oxidizing agent while maintaining the temperature at from about 0° C. to about 11° C.,
   g. agitating the reaction mass for an effective period of time and, during this period, preventing the temperature of the reaction mass from exceeding a temperature of about 20° C.,
   h. ramping the temperature of the reaction mass up to a temperature of from about 35° C. to about 40° C.,
   i. adjusting the pH with an organic acid such that the pH of the reaction mass is slightly acidic,
   j. adjusting the pH to about 6.6,
   k. ramping the temperature of the reaction mass up to a temperature of from about 55° C. to 59° C.,
   l. ramping the temperature down to a temperature of about 25 to about 30° C.,
   m. ramping, with agitation, the temperature of the reaction mass down to room temperature,
   n. filtering and washing the reaction mass with water and drying to a constant weight.

2. A process for the production of 3-iodo-2-propynyl butylcarbamate which comprises the steps of:
   a. charging a reaction vessel with an aqueous solution of a nonionic surfactant wherein the concentration of the nonionicsurfactant is from about 15 to about 20 weight percent based on the weight of the below set forth amount of n-propynyl butylcarbamate,
   b. cooling the solution to a temperature of from about 0 to about 8° C.,
   c. adding to the reaction mass a metal iodide salt which is a member selected from the group consisting of sodium iodide and potassium iodide,
   d. adjusting the pH of the reaction mass to greater than 7 with an alkali metal hydroxide and providing an excess of from about 0.8 to about 1.0 moles of alkali per mole of n-propynyl butylcarbamate to be added,
   e. while stirring, adding to the reaction mass a molar amount of n-propynyl butylcarbamate while maintaining the temperature of the reaction mass at from about 0 to about 8° C.,
   f. while stirring, charging the reaction mass with from about 1.1 to about 1.3 moles of sodium hypochlorite per mole of the metal iodide salt, while maintaining the temperature at from about 6 to about 11° C.,
   g. allowing the temperature of the reaction mass to ramp up to from about 15 to about 20° C. and continue the agitation for a period of time of from about 60 to about 120 minutes,
   h. ramping the temperature up to from about 35 to about 40° C. at a rate of from about 0.25 to about 0.75 degrees per minute,
   i. adjusting the pH of the reaction mass to about 6.9 with acetic acid,
   j. adjusting the pH to about 6.6 with sodium bisulfite
   k. ramping the temperature up to a temperature of from about 55 to about 59° C. at a rate of from about 0.25 to about 0.75 degrees per minute,
   l. ramping the temperatures of the reaction mass down to a temperature of from about 25 to about 30° C. at a rate of from about 0.35 to about 0.75 degrees per minute,
   m. washing the reaction mass with water, and
   n. drying the reaction mass at a temperature of from about 25 to about 45° C. to a constant weight.

3. A process for the production of 3-iodo-2-propynyl butylcarbamate comprising the steps of:
   a. charging a reaction vessel with an aqueous solution of a nonionic surfactant wherein the concentration of the nonionic surfactant is from about 15 to about 20 weight percent based on the weight of the below set forth amount of n-propynyl butylcarbamate,
   b. cooling the solution to a temperature of from about 0 to about 8° C.,
   c. adding to the reaction mass a metal iodide salt which is a member selected from the group consisting of sodium iodide and potassium iodide,
   d. adjusting the pH of the reaction mass to greater than 7 with an alkali metal hydroxide and providing an excess of from about 0.8 to about 1.0 moles of alkali per mole of the n-propynyl butylcarbamate to be added,
   e. while stirring, adding to the reaction mass a molar amount of n-propynyl butylcarbamate while maintaining the temperature from about 6 to about 11° C.,
   f. while stirring, charging the reaction mass with from about 1.1 to about 1.3 moles of sodium hypochlorite per mole of the metal iodide salt, while maintaining the temperature at from about 6 to about 11° C., g. allowing the temperature of the reaction mass to ramp up from about 15 to about 20° C. and continuing the stirring for a period of time of from about 60 to about 120 minutes,
h. ramping the temperature up to from about 35 to about 40° C., at a rate of from about 0.25 to about 0.75 degrees per minute,
i. adjusting the pH of the reaction mass to about 6.9 with acetic acid,
j. adjusting the pH to about 6.6 with sodium bisulfite
k. ramping the temperature up to a temperature from about 55 to about 59° C. at a rate of from about 0.25 to about 0.75 degrees per minute,
l. ramping the temperatures of the reaction mass down to a temperature from about 25 to about 30° C. at a rate of from about 0.35 to about 0.75 degrees per minute,
m. washing the reaction mass with water, and
n. drying the reaction mass at a temperature from about 25 to about 45° C. to a constant weight.

4. A process for the production of 3-iodo-2-propynyl butylcarbamate, comprising the steps of:
a. charging a reaction vessel with an aqueous solution of a nonionic surfactant wherein the concentration of the nonionic surfactant is from about 15 to about 20 weight percent based on the weight of the below set forth amount of n-propynyl butylcarbamate;
b. cooling the solution to a temperature of from about 0 to about 12° C.;
c. adding to the reaction mass a metal iodide salt;
d. adjusting the pH of the reaction mass to greater than 7 with an alkali metal hydroxide such that from about 0.8 to about 1.0 moles of alkali per mole of the n-propynyl butylcarbamate to be added is provided,
e. adding to the reaction mass a molar amount of n-propynyl butylcarbamate;
f. charging the reaction mass with an oxidizing agent while maintaining the temperature of the reaction mass at a temperature of from about 0 to about 11° C.,
g. preventing the temperature of the reaction mass from exceeding 20° C. while stirring for a period of time of from about 30 to about 180 minutes;
h. ramping the temperature of the reaction mass up to a temperature of from about 35 to about 40° C. at a rate of from about 0.25 to about 1.0° C. per minute,
i. adjusting the pH of the reaction mass to be slightly acidic;
j. adjusting the pH to about 6.6;
k. ramping the temperature of the reaction mass up to a temperature of from about 55 to about 59° C.;
l. ramping the temperatures of the reaction mass down to a temperature of from about 20 to about 30° C.;
m. washing the reaction mass with water; and
n. drying the reaction mass to a constant weight.

5. The process of claim 4, wherein in step (b) the solution is cooled to a temperature of from about 8 to about 10° C.

6. The process of claim 4, wherein in step (c) the metal iodide salt is selected from the group consisting of sodium iodide and potassium iodide.

7. The process of claim 4, wherein in step (d) the alkali metal hydroxide is selected from the group consisting of sodium hydroxide and potassium hydroxide.

8. The process of claim 4, wherein in step (f) the oxidizing agent is selected from the group consisting of sodium hypochlorite, potassium hypochlorite, and hydrogen peroxide.

9. The process of claim 4, wherein in step (f) the temperature of the reaction mass is maintained at a temperature of from about 4 to about 11° C.

10. The process of claim 4, wherein in step (g) the reaction mass is stirred for a period of time of from about 60 to about 120 minutes.

11. The process of claim 4, wherein in step (i) the pH is adjusted with an organic acid.

12. The process of claim 11, wherein the organic acid is acetic acid.

13. The process of claim 4, wherein in step (j) the pH is adjusted with a mild acid buffer.

14. The process of claim 13, wherein the mild acid buffer is sodium bisulfite.

15. The process of claim 4, wherein in step (k) the temperature is ramped up at a rate of from about 0.25 to about 0.75° C. per minute.

16. The process of claim 4, wherein in step (l) the temperature is ramped down at a rate of from about 0.25 to about 0.75° C. per minute.

17. The process of claim 4, wherein in step (m) the reaction mass is washed with water having a temperature of from about 10 to about 30° C.

18. The process of claim 4, wherein in step (n) the reaction mass is dried at a temperature of from about 25 to about 45° C.

* * * * *